(12) United States Patent
Ohsaka

(10) Patent No.: US 12,109,536 B2
(45) Date of Patent: Oct. 8, 2024

(54) PARTICLE CAPTURING DEVICE AND PARTICLE CAPTURING METHOD

(71) Applicant: TOKYO OHKA KOGYO CO., LTD., Kawasaki (JP)

(72) Inventor: Takashi Ohsaka, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 782 days.

(21) Appl. No.: 17/287,705

(22) PCT Filed: Oct. 30, 2019

(86) PCT No.: PCT/JP2019/042481
§ 371 (c)(1),
(2) Date: Apr. 22, 2021

(87) PCT Pub. No.: WO2020/090856
PCT Pub. Date: May 7, 2020

(65) Prior Publication Data
US 2021/0354087 A1    Nov. 18, 2021

(30) Foreign Application Priority Data

Nov. 2, 2018   (JP) ................. 2018-207706

(51) Int. Cl.
| | | |
|---|---|---|
| *B01D 61/14* | (2006.01) | |
| *B01D 61/18* | (2006.01) | |
| *B01D 61/20* | (2006.01) | |
| *B01D 63/08* | (2006.01) | |
| *B01L 3/00* | (2006.01) | |

(52) U.S. Cl.
CPC .......... *B01D 61/20* (2013.01); *B01D 61/147* (2013.01); *B01D 61/18* (2013.01); *B01D 63/088* (2013.01);
(Continued)

(58) Field of Classification Search
CPC ...... B01D 61/20; B01D 61/147; B01D 61/18; B01D 63/088; B01D 2221/10;
(Continued)

(56) References Cited

U.S. PATENT DOCUMENTS 3,678,607 A * 7/1972 Tabor ................... D05C 1/02
                                                      38/102.91
9,638,636 B2   5/2017 Tibbe et al.
(Continued)

FOREIGN PATENT DOCUMENTS

| CN | 105452439 A | 3/2016 |
|---|---|---|
| JP | 2012-076027 A | 4/2012 |

(Continued)

OTHER PUBLICATIONS

Office Action issued in European Patent Application No. 19879612.0, mailed Jul. 11, 2022.
(Continued)

*Primary Examiner* — Jill A Warden
*Assistant Examiner* — Michael Stanley Gzybowski
(74) *Attorney, Agent, or Firm* — Knobbe, Martens, Olson & Bear, LLP

(57) ABSTRACT

A particle capturing device including a substrate, a particle capturing film configured to capture particles, and a support configured to support the particle capturing film when tension is applied to the particle capturing film such that the particle capturing film is in parallel with the substrate and a space is formed between the particle capturing film and the substrate.

13 Claims, 12 Drawing Sheets

(52) U.S. Cl.
CPC .......... *B01L 3/505* (2013.01); *B01D 2221/10* (2013.01); *B01L 2200/0647* (2013.01); *B01L 2300/0609* (2013.01); *B01L 2300/123* (2013.01)

(58) Field of Classification Search
CPC ............. B01L 3/505; B01L 2200/0647; B01L 2300/0609; B01L 2300/123
See application file for complete search history.

(56) References Cited

U.S. PATENT DOCUMENTS

| | | |
|---|---|---|
| 2013/0149217 A1 | 6/2013 | Sim et al. |
| 2015/0004687 A1 | 1/2015 | Kikuhara et al. |
| 2016/0195458 A1 | 7/2016 | Kikuhara et al. |
| 2018/0282677 A1 | 10/2018 | Ohsaka et al. |
| 2020/0362294 A1 | 11/2020 | Suzuki et al. |

FOREIGN PATENT DOCUMENTS

| | | |
|---|---|---|
| JP | A-2013-138658 | 7/2013 |
| WO | WO 2015/019889 | 2/2015 |
| WO | WO 2017/051650 A1 | 3/2017 |
| WO | WO 2017/057234 A1 | 4/2017 |
| WO | WO 2018/105608 A1 | 6/2018 |

OTHER PUBLICATIONS

International Search Report in International Application No. PCT/JP2019/042481 mailed on Dec. 17, 2019.

* cited by examiner

PARTICLE CAPTURING DEVICE AND PARTICLE CAPTURING METHOD

TECHNICAL FIELD

The present invention relates to a particle capturing device and a particle capturing method.

Priority is claimed on Japanese Patent Application No. 2018-207706, filed Nov. 2, 2018, the content of which is incorporated herein by reference.

BACKGROUND ART

There is a demand for comprehensive analysis by capturing particles such as cells. For example, Patent Document 1 discloses a device including a film that is capable of capturing cells and a support structure that supports the film from below.

CITATION LIST

[Patent Document]
[Patent Document 1]
U.S. Pat. No. 9,638,636

SUMMARY OF INVENTION

Technical Problem

By the way, the film may be deflected depending on the weight of the film, the properties of the material, and the like. In a case where the film is deflected, defocusing occurs due to the influence of deflection in a case where captured particles are observed using a microscope.

In consideration of the above-described circumstances, an object of the present invention is to provide a particle capturing device and a particle capturing method which enable suppression of defocusing in a case where captured particles are observed.

Solution to Problem

According to an aspect of the present invention, there is provided a particle capturing device including: a substrate; a particle capturing film configured to capture particles; and a support configured to support the particle capturing film in a state of applying tension to the particle capturing film such that the particle capturing film is in parallel with the substrate and a space is formed between the particle capturing film and the substrate.

According to this configuration, since the tension is applied to the particle capturing film such that the particle capturing film is in parallel with the substrate and a space is formed between the particle capturing film and the substrate, it is possible to suppress deflection of the particle capturing film. Therefore, it is possible to suppress defocusing in a case where captured particles are observed. Further, in a case where the particle capturing device does not have a support structure for preventing deflection, it is possible to make an effective area for capturing particles as large as possible. Further, it is possible to suppress mounting of particles on the support structure. Further, it is possible to reduce the possibility that particles are erroneously recognized in a case of image analysis.

The particle capturing device may further include a fitting structure configured to allow the substrate and the support to be fitted to each other such that the tension is applied to the particle capturing film.

According to this configuration, it is possible to suppress deflection of the particle capturing film with a simple configuration using the fitting structure.

In the particle capturing device, the fitting structure may include a convex portion which is provided on the substrate, and a concave portion which is provided on the support and fitted to the convex portion.

According to this configuration, it is possible to suppress deflection of the particle capturing film with a simple configuration using the convex portion and the concave portion. Further, the particle capturing device is more easily prepared as compared to a case where the fitting structure includes a convex portion provided on the support and a concave portion provided on the substrate.

The particle capturing device may further include an expansion member configured to expand the support such that the tension is applied to the particle capturing film.

According to this configuration, it is possible to suppress deflection of the particle capturing film with a simple configuration using the expansion member.

The particle capturing device may further include a film expansion member configured to expand the particle capturing film such that the tension is applied to the particle capturing film.

According to this configuration, it is possible to suppress deflection of the particle capturing film with a simple configuration using the film expansion member.

The particle capturing device may further include an inclination support member configured to support the support in a state where the support is inclined with respect to the substrate such that the tension is applied to the particle capturing film.

According to this configuration, it is possible to suppress deflection of the particle capturing film with a simple configuration using the inclination support member.

The particle capturing device may further include a liquid-absorbing swelling member configured to be bonded to the support and increase in volume by absorbing a liquid such that the tension is applied to the particle capturing film.

According to this configuration, it is possible to suppress deflection of the particle capturing film with a simple configuration using the liquid-absorbing swelling member.

In the particle capturing device, the particle capturing film includes a capturing portion having a size which enables capturing of one particle, and a communication hole having a size which does not allow passage of one particle and allowing the capturing portion and the space to communicate with each other.

According to this configuration, it is possible to allow a dispersion liquid of particles to flow through the communication hole while capturing one particle by the capturing portion.

In the particle capturing device, the particle capturing film may include a first layer having the communication hole, and a second layer which is connected to the communication hole and has a through hole having the same size as that of an outer shape of the capturing portion. The particle capturing device is more easily prepared as compared to a case where the capturing portion and the communication hole are provided in a single layer.

In the particle capturing device, the space may be filled with a liquid.

According to this configuration, even in a case where the particle capturing film is immersed in a liquid, since the tension is applied to the particle capturing film, it is possible to suppress deflection of the particle capturing film depending on the swelling of the particle capturing film, the weight of the liquid, the influence of the surface tension, and the like.

According to an aspect of the present invention, there is provided a particle capturing method including: preparing a substrate, a particle capturing film which captures particles, and a support which supports the particle capturing film; and applying tension to the particle capturing film such that the particle capturing film is in parallel with the substrate and a space is formed between the particle capturing film and the substrate.

According to this method, since the tension is applied to the particle capturing film such that the particle capturing film is in parallel with the substrate and a space is formed between the particle capturing film and the substrate, it is possible to suppress deflection of the particle capturing film. Therefore, it is possible to suppress defocusing in a case where captured particles are observed. Further, in a case where the particle capturing device does not have a support structure for preventing deflection, it is possible to make an effective area for capturing particles as large as possible. Further, it is possible to suppress mounting of particles on the support structure.

DESCRIPTION OF EMBODIMENTS

Hereinafter, embodiments of the present invention will be described with reference to the accompanying drawings. In the following description, an XYZ orthogonal coordinate system is set, and the positional relationship of each member will be described with reference to the XYZ orthogonal coordinate system. A predetermined direction in a horizontal plane is defined as an X direction, a direction orthogonal to the X direction in the horizontal plane is defined as a Y direction, and a direction orthogonal to each of the X direction and the Y direction (that is, the vertical direction) is defined as a Z direction.

<Particle Capturing Device 1>

Figure 1:
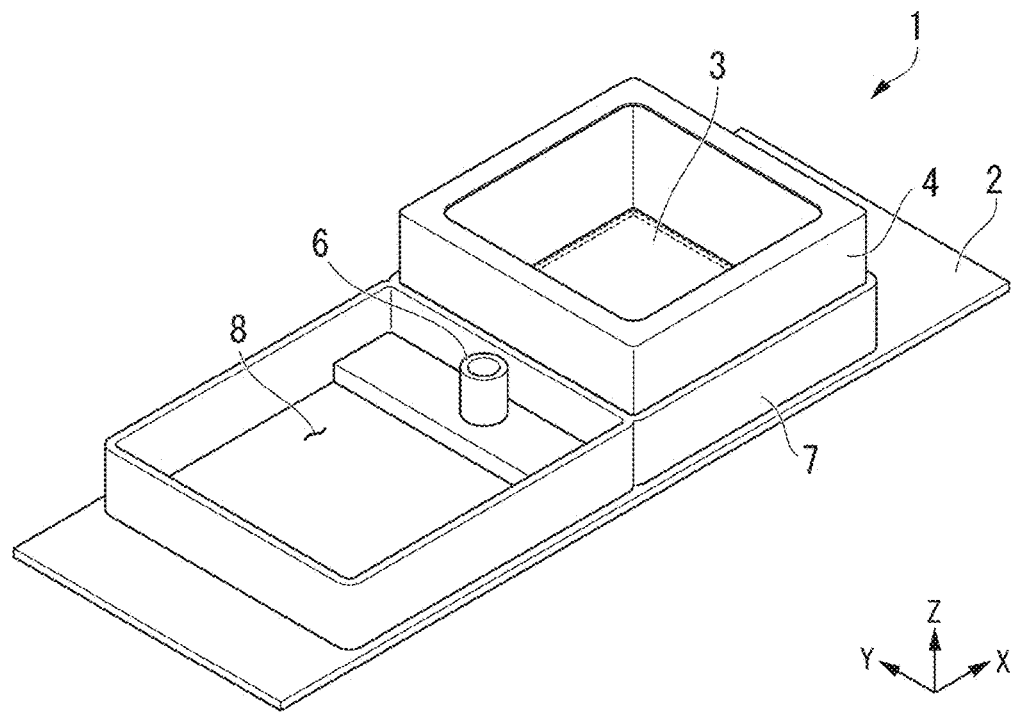
FIG. 1 is a perspective view showing a particle capturing device according to an embodiment.

FIG. 1 is a perspective view showing a particle capturing device 1 according to an embodiment.

As shown in FIG. 1, the particle capturing device 1 includes a substrate 2, a particle capturing film 3, a support 4, a fitting structure 5 (see FIG. 3), and a suction unit 6. The particle capturing device 1 forms a flow path 10 (space) of a dispersion medium of particles between the substrate 2 and the particle capturing film 3 (see FIG. 3). For example, the particle capturing device 1 is installed on a mounting surface parallel to the horizontal surface. In the figure, the reference numeral 7 represents a frame body holding the support 4, and the reference numeral 8 represents a waste liquid portion from which a liquid such as a dispersion medium is discharged.

<Particles>

Examples of the particles to be captured include cells, cell clusters, resin particles, metal particles, glass particles, and ceramic particles. Further, the particles to be captured are not limited thereto.

For example, the diameter of the particles may be approximately in a range of 1 to 500 μm, approximately in a range of 1 to 200 μm, approximately in a range of 1 to 100 μm, or approximately in a range of 1 to 50 μm. The diameter of a particle indicates the diameter of a circle having the same area as the projected area of the particle. Further, the diameter of a particle is not particularly limited.

<Dispersion Medium>

In a case of capturing particles, the particles are supplied to the particle capturing device 1 in a state of being suspended in a dispersion medium. An arrow W1 in FIG. 3 indicates a direction in which the particles in the state of being suspended in the dispersion medium are supplied.

Examples of the dispersion medium include water, a buffer solution, an isotonic solution, and a culture medium. Further, the dispersion medium is not particularly limited and can be appropriately used depending on the purpose thereof.

<Material>

From the viewpoint of facilitating observation of the particles, it is preferable that the material of the particle capturing device 1 is a material having transparency.

Further, in a case where the captured particles are observed using fluorescence observation as an index, it is preferable that the material thereof is a material with less autofluorescence. For example, as the material of the particle capturing device 1, a material having transparency and less autofluorescence can be used.

In a case where cells are captured as particles, it is preferable that the material of the particle capturing device 1 is a material that does not have cytotoxicity and has low adhesiveness to cells.

Further, the material of the particle capturing device 1 is not particularly limited, and various materials can be employed.

<Substrate 2>

Figure 2:
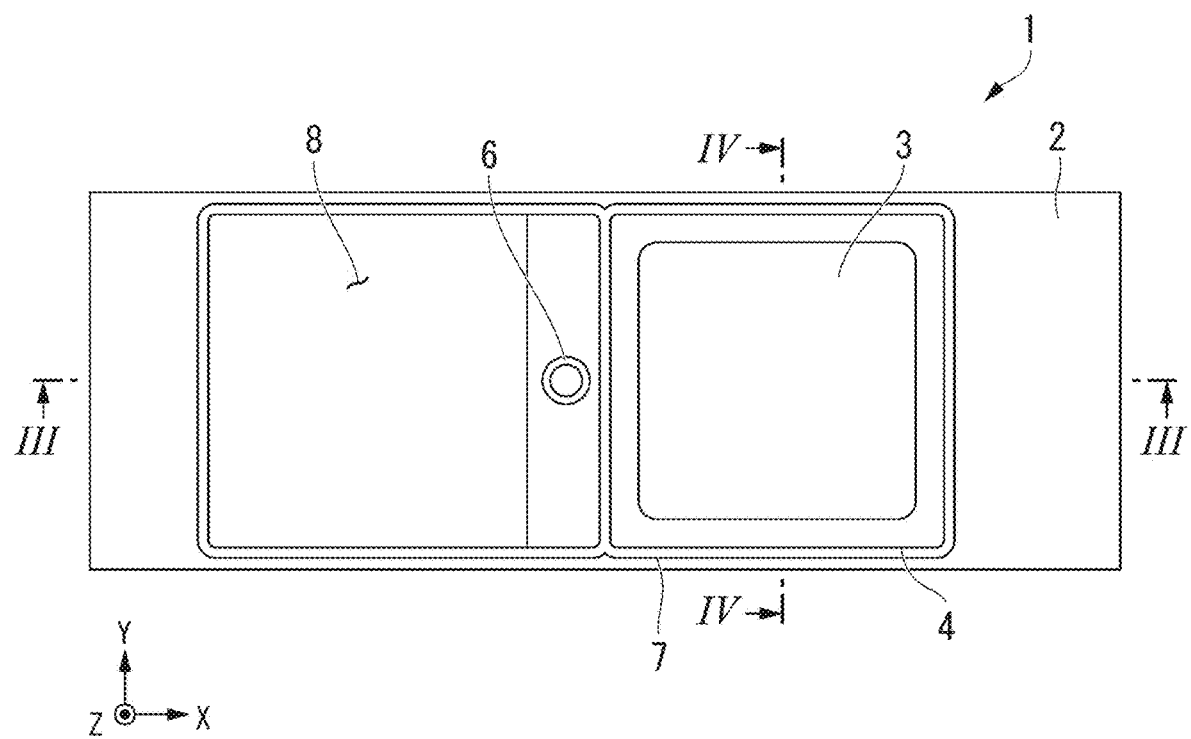
FIG. 2 is a top view showing the particle capturing device according to the embodiment.

As shown in FIG. 2, the substrate 2 has a rectangular plate shape. For example, the length of a long side of the substrate 2 is in a range of 50 mm to 100 mm. For example, the length of a short side of the substrate 2 is in a range of 10 mm to 40 mm.

For example, as the material of the substrate 2, a typical resin such as glass, polyethylene terephthalate (PET), polymethyl methacrylate (PMMA), polycarbonate (PC), polystyrene (PS), a cycloolefin polymer (COP), or epoxy can be used.

<Particle Capturing Film 3>

Figure 3:
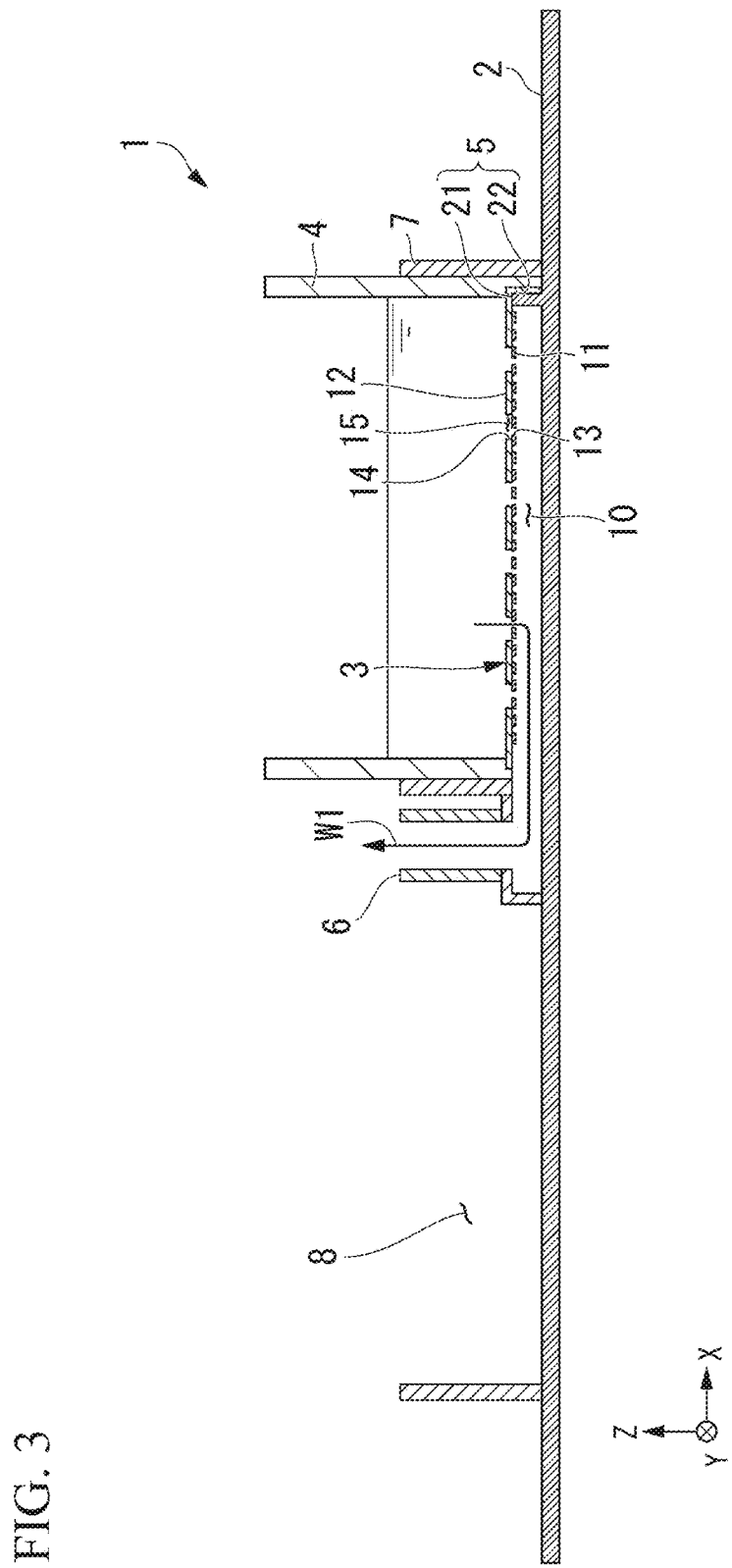
FIG. 3 is a view showing a cross section cut along line III-III of FIG. 2.
Figure 4:
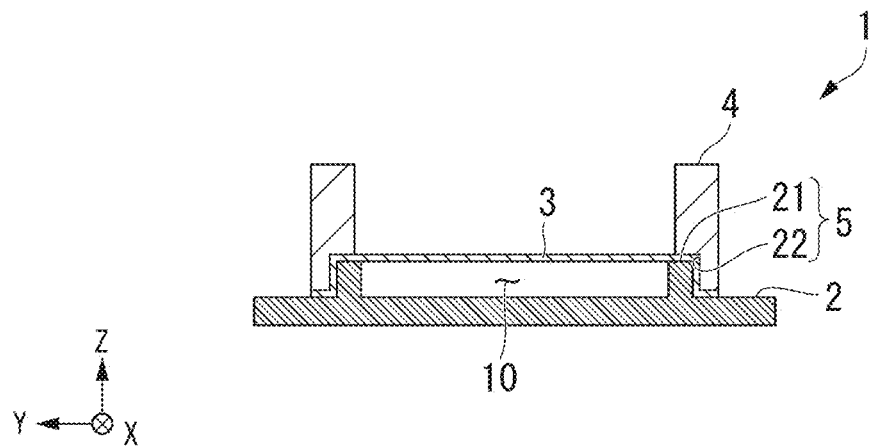
FIG. 4 is a view showing a cross section cut along line IV-IV of FIG. 2.
Figure 5:
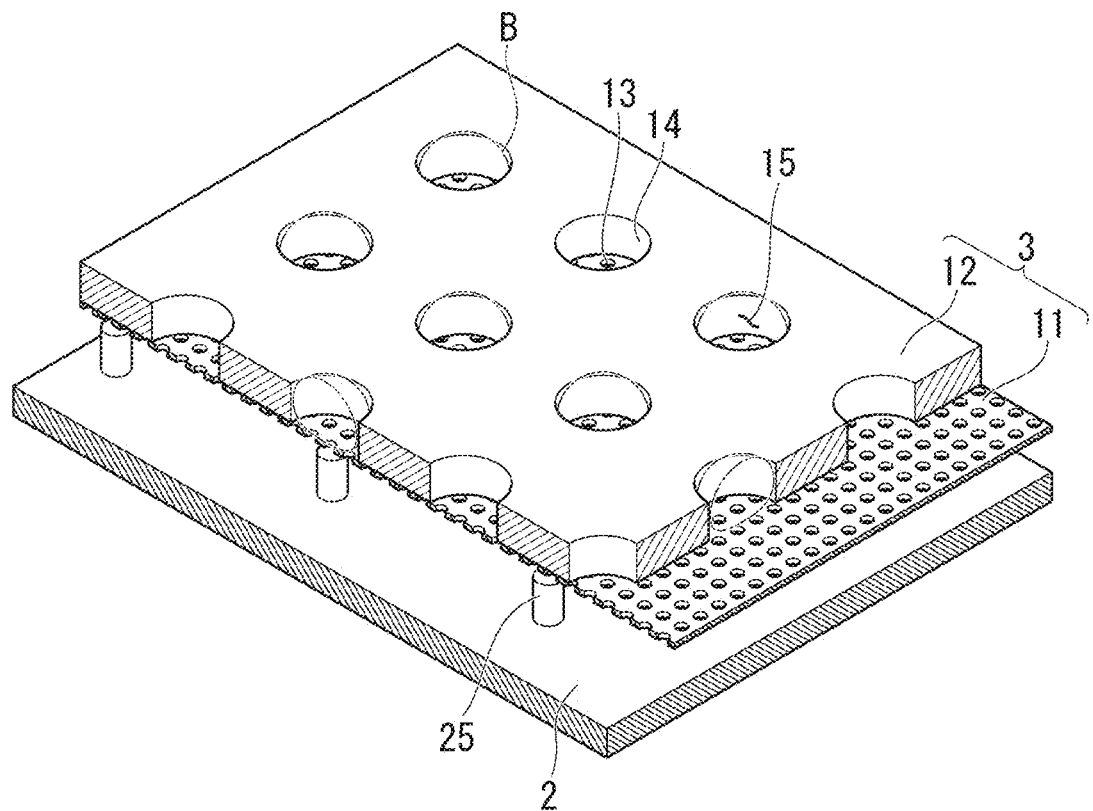
FIG. 5 is a perspective view showing an example of the particle capturing device.

The particle capturing film 3 is a film that is capable of capturing particles. As shown in FIG. 5, the particle capturing film 3 has a concave portion 15 (hereinafter, also referred to as a "capturing portion 15") having a size which enables capturing of one particle. The particle capturing film 3 includes a first layer 11 and a second layer 12. As shown in FIG. 3, the first layer 11 has a communication hole 13 that allows the capturing portion 15 and the flow path 10 to communicate with each other. The communication hole 13 has a size that does not allow passage of one particle. The second layer 12 has a through hole 14 connected to the communication hole 13. The through hole 14 has the same size as that of the outer shape of the capturing portion 15. The capturing portion 15 is formed of an upper surface of the first layer 11 (a surface facing the second layer 12) and the through hole 14 of the second layer 12. In FIG. 4, the laminated structure of the first layer 11 and the second layer 12, the capturing portion 15, the communication hole 13, and the like are not shown.

The reference numeral B in FIG. 5 represents one particle. In FIG. 5, the capturing portion 15 has a cylindrical shape.

The shape of the capturing portion 15 is not particularly limited as long as the shape enables capturing of one particle. For example, the shape of the capturing portion 15 may be a polyhedron formed of a plurality of surfaces (for example, a rectangular parallelepiped, a hexagonal column, or an octagonal column), an inverted conical trapezoidal shape, an inverted pyramid trapezoidal shape (for example, an inverted triangular pyramid trapezoidal shape, an inverted quadrangular pyramid trapezoidal shape, an inverted pentagonal pyramid trapezoidal shape, an inverted hexagonal pyramid trapezoidal shape, or an inverted heptagonal or higher polygonal pyramid trapezoidal shape), or a combination of two or more of these shapes. For example, the capturing portion 15 may be formed such that a part thereof has a cylindrical shape and the remaining part has an inverted conical trapezoidal shape. For example, in a case where the shape of the capturing portion 15 is a cylindrical shape or a rectangular parallelepiped, the bottom portion of the capturing portion 15 is typically flat, but may have a curved surface (a convex surface or a concave surface).

The dimensions of the capturing portion 15 can be appropriately determined in consideration of a suitable ratio between the diameter of particles intended to be captured by the capturing portion 15 and the dimensions of the capturing portion 15. It is preferable that the capturing portion 15 is patterned and the shape, the density, and the like are controlled. The shape and the dimensions of the capturing portion 15 are appropriately determined such that one particle is captured by one capturing portion 15 in consideration of the kind (the shape, the dimension, and the like of particles) of particles to be captured by the capturing portion 15.

In order for one capturing portion 15 to capture one particle, it is preferable that the dimensions of the capturing portion 15 are as follows. The diameter of the maximum circle inscribed in the planar shape of the capturing portion 15 is preferably in a range of 0.5 to 2 times the diameter of the particles intended to be captured by the capturing portion 15, more preferably in a range of 0.8 to 1.9 times the diameter thereof, and still more preferably in a range of 0.8 to 1.8 times the diameter thereof. The depth of the capturing portion 15 is preferably in a range of 0.5 to 4 times the diameter of the particles intended to be captured by the capturing portion 15, more preferably in a range of 0.8 to 1.9 times the diameter thereof, and still more preferably in a range of 0.8 to 1.8 times the diameter thereof.

For example, in a case where the particles intended to be captured have a substantially spherical shape with a diameter of approximately 1 to 50 μm, it is preferable that the thickness of the particle capturing film 3, the number of capturing portions 15, and the dimensions of the capturing portion 15 are as follows.

The thickness of the particle capturing film 3 is preferably in a range of 1 to 100 μm and more preferably in a range of 10 to 50 μm.

The number of capturing portions 15 included in the particle capturing film 3 is preferably in a range of 2,000 to 1,000,000 per 1 cm².

For example, in a case where the capturing portion 15 has a cylindrical shape, in the dimensions of the capturing portion 15, the diameter thereof is preferably in a range of 1 to 100 μm, more preferably in a range of 2 to 50 μm, and still more preferably in a range of 3 to 25 μm. The depth of the capturing portion 15 is preferably in a range of 1 to 100 μm, more preferably in a range of 2 to 70 μm, still more preferably in a range of 3 to 50 μm, and particularly preferably in a range of 4 to 30 μm. It is preferable that the depth of the capturing portion 15 is 1 μm or greater from the viewpoints of practical applications and easily capturing particles. It is preferable that the depth of the capturing portion 15 is 100 μm or less from the viewpoint that the possibility of capturing a plurality of particles is low.

The dimensions of the communication holes 13 can be appropriately determined in consideration of the diameter of the particles intended to be captured by the capturing portion 15, the dimensions of the capturing portion 15, the characteristics of the dispersion medium of the particles which moves through the communication holes 13, and the like. It is preferable that the communication holes 13 are patterned and the form, the diameter of the pores, the density thereof, and the like are controlled. It is preferable that the communication holes 13 are controlled from the viewpoint that the uniformity in amount of the dispersion medium of the particles to permeate is easily ensured. The communication holes 13 are not limited to those prepared by patterning. For example, the communication holes 13 may be formed of a porous material such as a porous film.

The number, the position, the shape, the size, and the like of the communication holes 13 are not particularly limited as long as particles can be captured (stored inside the capturing portion 15) without passing through the communication holes and the communication holes have a size that enables the dispersion medium to move.

For example, in a case where the capturing portion 15 has a cylindrical shape, a plurality of circular communication holes 13 having a diameter smaller than the diameter of the capturing portion 15 may be provided at the bottom portion of the capturing portion 15. The shape of the communication holes 13 is not limited to the circular shape. For example, the shape of the communication holes 13 may be a rectangular shape.

For example, in a case where the particles intended to be captured have a substantially spherical shape with a diameter of approximately 1 to 50 μm and the communication holes 13 have a circular shape, the diameter of the communication holes 13 is preferably in a range of 10 nm to 20 μm, more preferably in a range of 50 nm to 15 μm, and still more preferably in a range of 100 nm to 10 μm. In a case where the communication holes 13 have a rectangular shape, the length of one side is preferably in a range of 10 nm to 20 μm, more preferably in a range of 50 mu to 15 μm, and still more preferably in a range of 100 nm to 10 μm.

As the material of the particle capturing film 3, it is preferable to use a material having flexibility from the viewpoint of preventing cracking. For example, the material of the particle capturing film 3 is a polymer such as a synthetic resin. Since the particle capturing film 3 has fine structures such as the capturing portion 15 and the communication holes 13, in a case where the material of the particle capturing film 3 is silicon nitride (SiN), cracks easily occur in the film in a case of a decrease in film thickness. On the contrary, in a case where the material of the particle capturing film 3 is a polymer, cracks are unlikely to occur in a case of a decrease in film thickness.

<Flow Path 10>

As shown in FIG. 3, the flow path 10 has the communication hole 13 of the particle capturing film 3 as an inflow port and the suction unit 6 as an outflow port. By sucking the dispersion medium from the suction unit 6, the dispersion medium flows through the flow path 10 in a direction of the arrow W1 in FIG. 3.

For example, in a case where the particles intended to be captured have a substantially spherical shape with a diameter of approximately 1 to 50 μm, the distance between the substrate 2 and the particle capturing film 3 may be 100 μm or greater, 150 μm or greater, 200 μm or greater, 250 μm or greater, 300 μm or greater, or 350 μm or greater. The upper limit of the distance between the substrate 2 and the particle capturing film 3 is not limited to the performance of the particle capturing device 1. In consideration of the practicality of the particle capturing device 1 (the amount of the dispersion medium to be used, the size of the microscope to be used for observation, and the like), the distance between the substrate 2 and the particle capturing film 3 is preferably 5 mm or less.

<Support 4>

The support 4 supports the particle capturing film 3 in a state of applying tension to the particle capturing film 3 such that the particle capturing film 3 is in parallel with the substrate 2 and the space 10 is formed between the particle capturing film 3 and the substrate 2. The concept of the particle capturing film 3 being in parallel with the substrate 2 includes the particle capturing film 3 being in substantially parallel with the substrate 2 in consideration of production variations, the dimensional tolerance, and the like of the particle capturing device 1.

The support 4 has a rectangular frame shape. Further, the shape of the support 4 is not particularly limited as long as the shape enables the support 4 to support the particle capturing film 3.

For example, as the material of the support 4, the same resin as that of the substrate 2 can be used. The space 10 between the particle capturing film 3 and the substrate 2 serves as the flow path 10 through which the dispersion medium of the particles flows. The space 10 is filled with a dispersion medium (liquid).

<Fitting Structure 5>

The fitting structure 5 allows the substrate 2 and the support 4 to be fitted to each other such that the tension is applied to the particle capturing film 3. The fitting structure 5 includes a convex portion 21 and a concave portion 22 that are fitted to each other. The fitting structure 5 is provided between the substrate 2 and the support 4.

The convex portion 21 is provided on the substrate 2. The convex portion 21 protrudes upward from the upper surface of the substrate 2. For example, the convex portion 21 is formed of the same member as that of the substrate and integrated with the substrate 2.

The concave portion 22 is provided inside a lower portion of the support 4. For example, the convex portion 21 is press-fitted into the concave portion 22 of the support 4 together with the particle capturing film 3. In this manner, the particle capturing film 3 can be supported in a state where the tension is applied to the particle capturing film 3.

<Method of Producing Particle Capturing Device 1>

A method of producing the particle capturing device 1 includes a preliminary step of preparing the substrate 2, the particle capturing film 3, and the support 4; and a tension application step of applying the tension to the particle capturing film 3.

From the viewpoint of forming the capturing portion 15 having a size that enables capturing of one particle and the communication hole 13 having a size that enables the dispersion medium to move therethrough, it is preferable that the material of the particle capturing device 1 is obtained by polymerization using a curable resin composition that can be easily microfabricated (hereinafter, also referred to as a "photosensitive resin composition").

The curable resin composition has a property that the composition is crosslinked and cured by being irradiated with active energy rays such as ultraviolet rays, and it is preferable that the curable resin composition is used for a negative-type photoresist, a negative-type dry film resist, molding a fine resin having a fine structure, and the like. Hereinafter, a cured product obtained by curing a curable resin composition into a desired shape according to a photolithography method will also be referred to as a resin pattern.

In a case where the curable resin composition is used for applications such as fine resin molding, first, a surface of a base material on which a resin pattern is formed is coated with the curable resin composition, and a solvent component contained in the curable resin composition is volatilized to prepare a resin film. Next, a photomask in a shape of the pattern to be formed is placed on the surface of the resin film, and the surface thereof is irradiated with active energy rays such as ultraviolet rays. Thereafter, the resin pattern is formed on the surface of the base material by performing a development step and, as necessary, a post-baking step. This resin pattern can be used for the particle capturing device 1 according to the present embodiment.

As such a curable resin composition, a resin composition typically used for fine resin molding, such as a photocurable composition which contains an epoxy functional novolak resin, a cationic photopolymerization initiator such as a triarylsulfonium salt, and a diluent capable of reacting with an epoxy functional group and is completely cured to form a resin that is unlikely to be peeled off; or a photocurable composition which contains a polyfunctional bisphenol A formaldehyde-novolak resin, triphenylsulfonium hexafluoroantimonate serving as an acid generator, and PGMEA which is a solvent and is used to form a resin capable of forming a thick film, can be employed.

Further, in a case where a curable resin composition is prepared by combining an epoxy resin and a specific acid generator and a resin pattern is formed using this curable resin composition, a resin pattern in the form having a high sensitivity, small volume shrinkage during the heating and curing of the composition, and a high aspect ratio can be formed.

In addition, the details of the curable resin composition and this implementation are readily understood by those skilled in the art based on the methods known to those skilled in the art, described in Japanese Unexamined Patent Application, First Publication Nos. 2008-180877 and 2011-111588.

<Preliminary Step>

The preliminary step includes a particle capturing film preparation step, a substrate preparation step, and a support preparation step.

The particle capturing film preparation step includes a first layer formation step of forming the first layer 11 and a second layer formation step of forming the second layer 12.

Figure 6A:
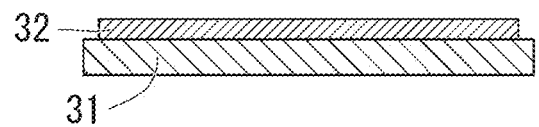
FIG. 6A is an explanatory view showing a step of forming a base film in a method of preparing a particle capturing film according to an embodiment.
Figure 6B:
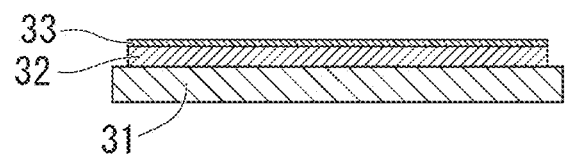
FIG. 6B is an explanatory view showing a step of forming a first curable resin film in the method of preparing a particle capturing film according to the embodiment.
Figure 6C:
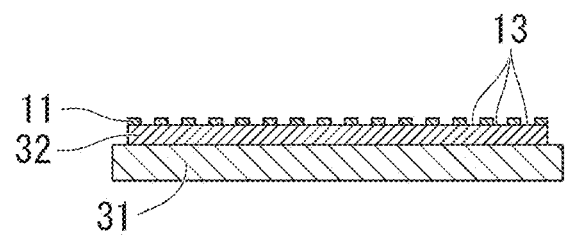
FIG. 6C is an explanatory view showing a step of forming a first layer in the method of preparing a particle capturing film according to the embodiment.

In the first layer formation step, a base film 32 which can be melted is formed on a support plate 31 (see FIG. 6A). Next, the base film 32 is coated with a first curable resin composition to form a first curable resin film 33 (see FIG. 6B). Next, the first curable resin film 33 is exposed to light and developed, thereby forming the first layer 11 in which the communication holes 13 are patterned (see FIG. 6C).

Further, in the first layer formation step, the support plate 31 may be directly coated with the first curable resin composition to form the first curable resin film 33 without forming the base film 32 on the support plate 31.

Examples of the support plate 31 include a metal substrate such as a silicon wafer, copper, chromium, iron, or aluminum; and a glass substrate. Examples of the first curable resin composition include the photosensitive resin composition described above.

For example, as the base film 32, a polyvinyl alcohol resin, dextrin, gelatin, glue, casein, shellac, gum arabic, starch, protein, polyacrylic acid amide, sodium polyacrylate, polyvinyl methyl ether, a styrene-based elastomer, a copolymer of methyl vinyl ether and maleic anhydride, a copolymer of vinyl acetate and itaconic acid, polyvinylpyrrolidone, acetyl cellulose, hydroxyethyl cellulose, or sodium alginate can be used. These materials may be a combination of a plurality of materials that are soluble in the same kind of liquid. For example, the material of the base film 32 may contain a rubber component such as mannan, xanthan gum, or guar gum from the viewpoints of the hardness and the flexibility of the base film 32.

The method of patterning the communication holes 13 is not limited to light exposure and development, and an imprint method or a method using a directed self assembly (DSA) technique can also be employed. Further, the method of curing the first curable resin film 33 is not limited to light exposure, and a known method may be employed.

Figure 6D:
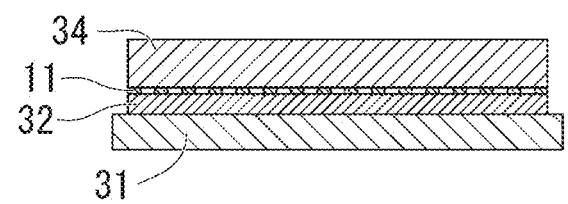
FIG. 6D is an explanatory view showing a step of forming a second curable resin film in the method of preparing a particle capturing film according to the embodiment.
Figure 6E:
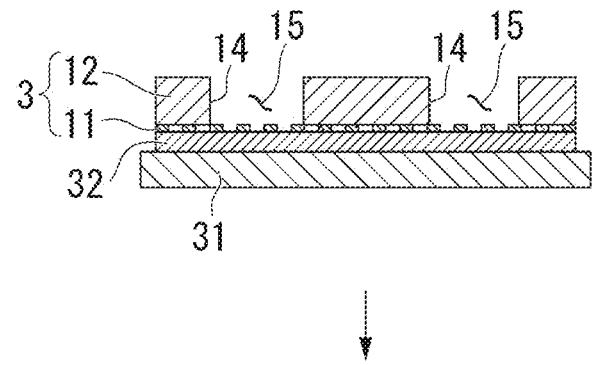
FIG. 6E is an explanatory view showing a step of forming a second layer in the method of preparing a particle capturing film according to the embodiment.

In the second layer formation step, the first layer 11 is coated with a second curable resin composition to form a second curable resin film 34 (see FIG. 6D). Next, the second curable resin film 34 is exposed to light and developed, thereby forming a second layer 12 in which through holes 14 (capturing portions 15) are patterned (see FIG. 6E).

Examples of the second curable resin composition include the photosensitive resin composition described above.

The method of patterning the capturing portions 15 is not limited to light exposure and development, and an imprint method or a method using a directed self assembly (DSA) technique can also be employed. Further, the method of curing the second curable resin composition is not limited to light exposure, and a known method may be employed.

After the second layer formation step, the first layer 11 is peeled from the support plate 31 by melting the base film 32.

Figure 6F:
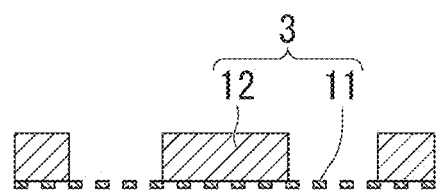
FIG. 6F is an explanatory view showing the particle capturing film in the method of preparing a particle capturing film according to the embodiment.

For example, the base film 32 is melted by immersing the entire support plate 31 in a release agent so that the first layer 11 is peeled from the support plate 31. In this manner, the particle capturing film 3 is obtained (see FIG. 6F). Further, the support plate 31 may be melted after the second layer formation step. The support 4 may be bonded to the particle capturing film 3 before the first layer 11 is peeled off from the support plate 31.

In the substrate preparation step, the convex portion 21 that can be fitted to the concave portion 22 of the support 4 is formed on the substrate 2. For example, in the substrate preparation step, the convex portion 21 is formed on the substrate 2 by performing injection molding.

In the substrate preparation step, pillars 25 may be formed on the substrate 2. For example, in the substrate preparation step, the pillars 25 are formed on the substrate 2 by performing injection molding. Further, a pillar pattern may be formed by performing the same steps as those in the formation of the convex portion 21. The formation of the pillar pattern 22 is optional, and the present step may not be present.

In the support preparation step, the concave portion 22 that is fitted to the convex portion 21 of the substrate 2 is formed in a portion (the lower portion of the support 4) of the support 4 that faces the substrate 2. For example, in the support preparation step, the concave portion 22 is formed, by performing injection molding, inside (inside the lower portion of the support 4) the surface (the lower surface of the support 4) of the support 4 which faces the substrate 2.

<Tension Application Step>

Figure 7A:
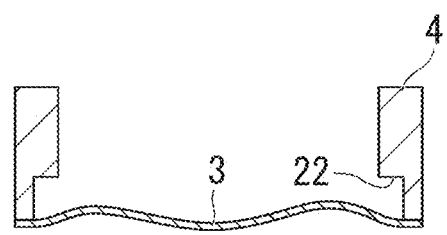
FIG. 7A is an explanatory view showing the particle capturing film before a tension application step in a method of producing a particle capturing device according to an embodiment.
Figure 7B:
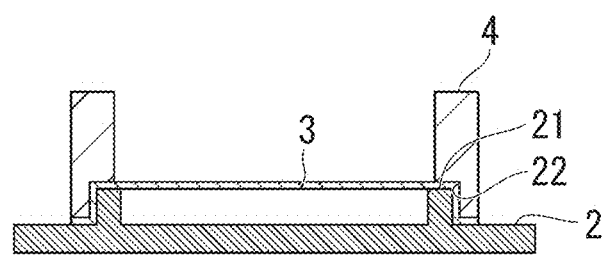
FIG. 7B is an explanatory view showing a fitting step of allowing a convex portion of a substrate and a concave portion of a support to be fitted to each other in the method of producing a particle capturing device according to the embodiment.

In the tension application step, the tension is applied to the particle capturing film 3 such that the particle capturing film 3 is in parallel with the substrate 2 and the space 10 is formed between the particle capturing film 3 and the substrate 2 (see FIG. 7A and FIG. 7B). The deflection of the particle capturing film 3 before the tension application step is exaggerated in FIG. 7A, but the present invention is not limited thereto. Before the tension application step, the particle capturing film 3 may not be deflected.

In the tension application step, the substrate 2 and the support 4 are fitted to each other such that the tension is applied to the particle capturing film 3. For example, the tension application step includes a film bonding step of bonding the particle capturing film 3 to the support 4 (see FIG. 7A) and a fitting step of fitting the support 4, to which the particle capturing film 3 is bonded, to the substrate 2 after the film bonding step. Specifically, in the fitting step, the concave portion 22 provided in the support 4 to which the particle capturing film 3 is bonded is fitted to the convex portion 21 provided on the substrate 2 (see FIG. 7B). For example, the particle capturing film 3 can be supported in a state in which the tension is applied to the particle capturing film 3 by press-fitting the convex portion 21 and the particle capturing film 3 into the concave portion 22 of the support 4.

In this manner, the substrate 2, the particle capturing film 3, and the support 4 can be bonded to each other in a state where the tension is applied to the particle capturing film 3. For example, the curable resin composition may be used as an adhesive.

<Particle Capturing Method>

In an embodiment, the present invention provides a particle capturing method including: preparing the substrate 2, the particle capturing film 3 capable of capturing particles, and the support 4 which supports the particle capturing film 3, and applying the tension to the particle capturing film 3 such that the particle capturing film 3 is in parallel with the substrate 2 and the space 10 is formed between the particle capturing film 3 and the substrate 2. The particle capturing method of the embodiment can also be referred to as a method including a preliminary step of preparing the substrate 2, the particle capturing film 3, and the support 4 and a tension application step of applying the tension to the particle capturing film 3 or a method of producing the particle capturing device 1, including a preliminary step and a tension application step.

As described above, according to the present embodiment, the particle capturing device 1 includes the substrate 2, the particle capturing film 3 capable of capturing particles, and the support 4 which supports the particle capturing film 3 in a state of applying the tension to the particle capturing film 3 such that the particle capturing film 3 are in parallel with the substrate 2 and the space 10 is formed between the particle capturing film 3 and the substrate 2, and thus the following effects are exerted.

According to this configuration, since the tension is applied to the particle capturing film 3 such that the particle capturing film 3 is in parallel with the substrate 2 and the space 10 is formed between the particle capturing film 3 and the substrate 2, deflection of the particle capturing film 3 can be suppressed. Therefore, it is possible to suppress defocusing in a case where captured particles are observed. Further, in a case where the particle capturing device does not have a support structure for preventing deflection, it is possible to make an effective area for capturing particles as large as possible. Further, it is possible to suppress mounting of particles on the support structure. Further, it is possible to reduce the possibility that particles are erroneously recognized in a case of image analysis.

The particle capturing device 1 has the fitting structure 5 of allowing the substrate 2 and the support 4 to be fitted to each other such that the tension is applied to the particle capturing film 3, and thus the following effects are exerted.

According to this configuration, it is possible to suppress deflection of the particle capturing film 3 with a simple configuration using the fitting structure 5.

In the particle capturing device 1, the fitting structure 5 includes the convex portion 21 provided on the substrate 2 and the concave portion 22 provided in the support 4 and fitted to the convex portion 21, and thus the following effects are exerted.

According to this configuration, it is possible to suppress deflection of the particle capturing film 3 with a simple configuration using the convex portion 21 and the concave portion 22. In addition, the particle capturing device 1 is more easily prepared as compared to a case where the fitting structure 5 includes the convex portion 21 provided on the support 4 and the concave portion 22 provided on the substrate 2.

In the particle capturing device 1, the particle capturing film 3 includes the capturing portion 15 having a size that enables capturing of one particle and the communication hole 13 which has a size that does not allow passage of one particle and allows the capturing portion 15 and the space 10 to communicate with each other, and thus the following effects are exerted.

According to this configuration, the dispersion liquid of the particles can flow through the communication hole 13 while one particle is captured by the capturing portion 15.

In the particle capturing device 1, the particle capturing film 3 includes the first layer 11 having the communication hole 13 and the second layer 12 which is connected to the communication hole 13 and has the through hole 14 having the same size as that of the outer shape of the capturing portion 15, and thus the following effects are exerted.

According to this configuration, the particle capturing device 1 is more easily prepared as compared to a case where the capturing portion 15 and the communication hole 13 are provided in a single layer.

In the particle capturing device 1, the space 10 is filled with a liquid, and thus the following effects are exerted.

According to this configuration, even in a case where the particle capturing film 3 is immersed in a liquid, since the tension is applied to the particle capturing film 3, it is possible to suppress deflection of the particle capturing film 3 depending on the swelling of the particle capturing film 3, the weight of the liquid, the influence of the surface tension, and the like.

First Modified Example

Next, a first modified example of an embodiment will be described with reference to FIGS. 8, 9A, and 9B.

In the first modified example, the configuration for applying the tension to the particle capturing film 3 is particularly different from the configurations of the embodiments described above. In FIGS. 8, 9A, and 9B, the same configurations as those of the embodiments described above are denoted by the same reference numerals, and the detailed description thereof will not be provided.

Figure 8:
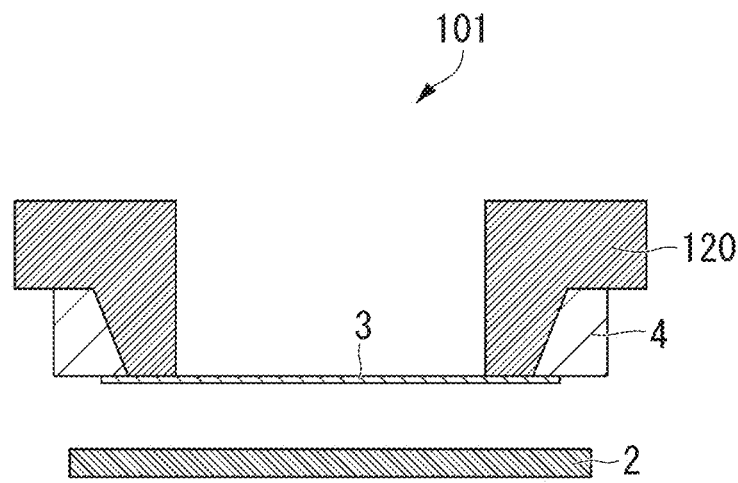
FIG. 8 is a cross-sectional view showing a particle capturing device according to a first modified example of an embodiment.
Figure 9A:
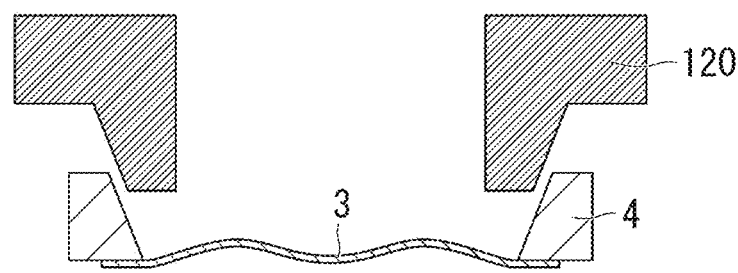
FIG. 9A is an explanatory view showing a particle capturing film before a tension application step in the method of producing a particle capturing device according to the first modified example of the embodiment.
Figure 9B:
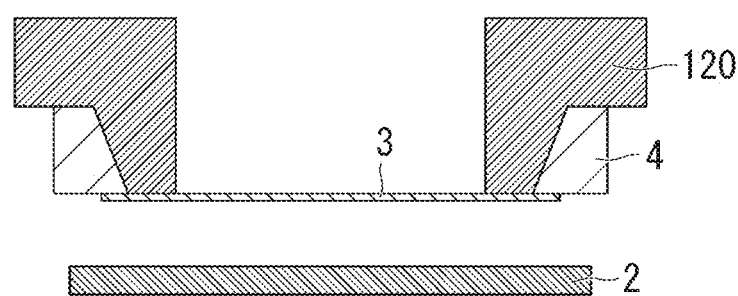
FIG. 9B is an explanatory view showing a step of bonding an expansion member and a support to each other in the method of producing a particle capturing device according to the first modified example of the embodiment.

FIG. 8 is a cross-sectional view showing a particle capturing device 101 according to the first modified example of the embodiment. FIG. 8 is a view corresponding to FIG. 4.

As shown in FIG. 8, the particle capturing device 101 includes an expansion member 120 which expands the support 4 by being bonded to the support 4 and being press-fitted thereto such that the tension is applied to the particle capturing film 3. The expansion member 120 is attached to the inside of the support 4. The expansion member 120 expands the support 4 from the inner surface. The expansion member 120 supports the support 4 from the inside. An outer surface of a lower portion of the expansion member 120 is inclined such that the upper end is positioned outward and the lower end is positioned inward. An inner surface of the support 4 according to the first modified example is inclined such that the upper end is positioned outward and the lower end is positioned inward. Further, in a case where the expansion member 120 can be press-fitted, the outer surface of the expansion member 120 may not be inclined, and the inner surface of the support 4 may not be inclined. The inner shape of the support 4 of the first modified example is smaller than the expansion member 120 before the expansion member 120 is attached to the support 4 (see FIG. 9A). The support 4 of the first modified example is connected to the substrate 2 by a connection member (not shown) such that the space 10 is formed between the particle capturing film 3 and the substrate 2.

In the first modified example, in the tension application step, the tension is applied to the particle capturing film 3 such that the particle capturing film 3 is in parallel with the substrate 2 and the space 10 is formed between the particle capturing film 3 and the substrate 2. The deflection of the particle capturing film 3 before the tension application step is exaggerated in FIG. 9A, but the present invention is not limited thereto. Before the tension application step, the particle capturing film 3 may not be deflected.

In the tension application step, the support 4 is expanded by press-fitting the expansion member 120 to the support 4 to which the particle capturing film 3 is bonded such that the tension is applied to the particle capturing film 3. Specifically, the outer surface of the expansion member 120 is bonded to the inner surface of the support 4 by press-fitting the expansion member 120 to the support 4 (see FIG. 9B). For example, the curable resin composition may be used as an adhesive.

According to the present modified example, the particle capturing device 101 includes the expansion member 120 that expands the support 4 such that the tension is applied to the particle capturing film 3, and thus the following effects are exerted.

According to this configuration, it is possible to suppress deflection of the particle capturing film 3 with a simple configuration using the expansion member 120.

Second Modified Example

Next, the first modified example of the embodiment will be described with reference to FIGS. 10, 11A, and 11B.

In the second modified example, the configuration for applying the tension to the particle capturing film 3 is particularly different from the configurations of the embodiments described above. In FIGS. 10, 11A, and 11B, the same configurations as those of the embodiments described above are denoted by the same reference numerals, and the detailed description thereof will not be provided.

Figure 10:
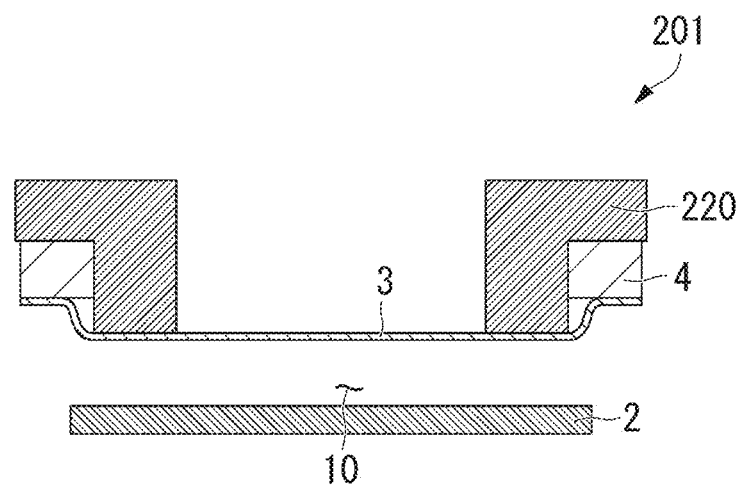
FIG. 10 is a cross-sectional view showing a particle capturing device according to a second modified example of an embodiment.
Figure 11A:
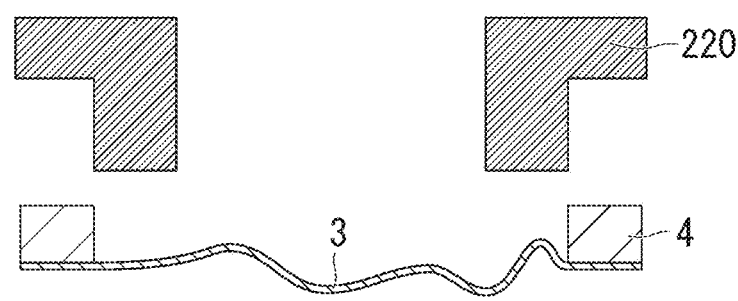
FIG. 11A is an explanatory view showing a particle capturing film before a tension application step in a method of producing a particle capturing device according to the second modified example of the embodiment.
Figure 11B:
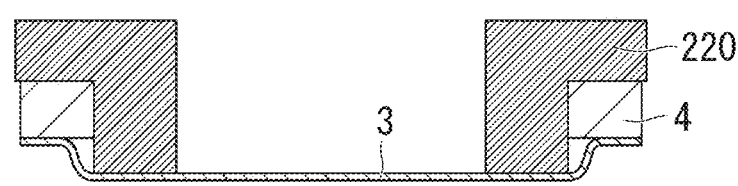
FIG. 11B is an explanatory view showing a step of bonding a film expansion member and a support to each other in the method of producing a particle capturing device according to the second modified example of the embodiment.

FIG. 10 is a cross-sectional view showing a particle capturing device 201 according to the second modified example of the embodiment. FIG. 10 is a view corresponding to FIG. 4.

As shown in FIG. 10, the particle capturing device 201 includes a film expansion member 220 which expands the particle capturing film 3 by being bonded to the support 4 and being press-fitted thereto such that the tension is applied to the particle capturing film 3. The film expansion member 220 is attached to the inside of the support 4. The film expansion member 220 expands the particle capturing film 3 from the inner surface. The film expansion member 220 supports the support 4 from the inside. The cross-sectional shape of the film expansion member 220 is an L shape. In a case where the support 4 can be supported from the inside, the cross-sectional shape of the film expansion member 220 may not be an L shape.

An outer surface of a lower portion of the film expansion member 220 has an outer shape that enables the particle capturing film 3 to expand. The inner shape of the support 4 of the second modified example is smaller than the film expansion member 220 before the film expansion member 220 is attached to the support 4 (see FIG. 11A). Further, in a case where the film expansion member 220 can be supported, the inner shape of the support 4 may be smaller than the film expansion member 220. Further, in a case where the particle capturing film 3 can be expanded, the inner shape of the support 4 may not be smaller than the film expansion member 220.

The height of the support 4 of the second modified example is lower than the height of the outer surface of the lower portion of the film expansion member 220. The support 4 of the second modified example is connected to the substrate 2 by a connection member (not shown) such that the space 10 is formed between the particle capturing film 3 and the substrate 2.

In the second modified example, in the tension application step, the tension is applied to the particle capturing film 3 such that the particle capturing film 3 is in parallel with the substrate 2 and the space 10 is formed between the particle capturing film 3 and the substrate 2. The deflection of the particle capturing film 3 before the tension application step is exaggerated in FIG. 11A, but the present invention is not limited thereto. Before the tension application step, the particle capturing film 3 may not be deflected.

In the tension application step, the particle capturing film 3 is expanded by press-fitting the film expansion member 220 to the support 4 to which the particle capturing film 3 is bonded such that the tension is applied to the particle capturing film 3. Specifically, the outer surface of the film expansion member 220 is bonded to the inner surface of the support 4 by press-fitting the film expansion member 220 to the support 4 (see FIG. 11B). In the second modified example, the lower end portion of the film expansion member 220 protrudes downward from the lower surface of the support 4 (see FIG. 11B). For example, the curable resin composition may be used as an adhesive.

According to the present modified example, the particle capturing device 201 includes the film expansion member 220 that expands the particle capturing film 3 such that the tension is applied to the particle capturing film 3, and thus the following effects are exerted.

According to this configuration, it is possible to suppress deflection of the particle capturing film 3 with a simple configuration using the film expansion member 220.

Third Modified Example

Next, a third modified example of an embodiment will be described with reference to FIGS. 12, 13A, and 13B.

In the third modified example, the configuration for applying the tension to the particle capturing film 3 is particularly different from the configurations of the embodiments described above. In FIGS. 12, 13A, and 13B, the same configurations as those of the embodiments described above are denoted by the same reference numerals, and the detailed description thereof will not be provided.

Figure 12:
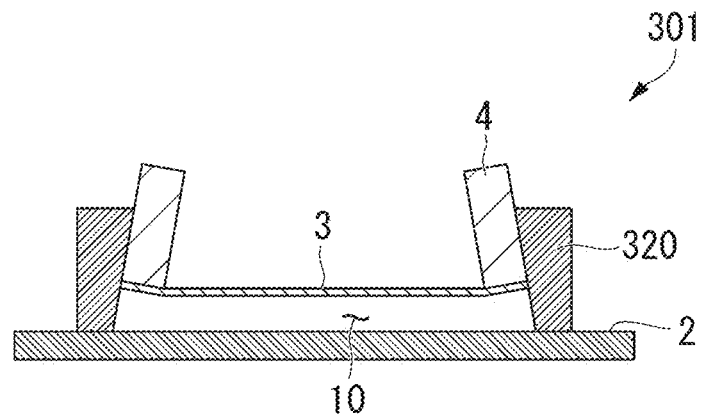
FIG. 12 is a cross-sectional view showing a particle capturing device according to a third modified example of an embodiment.
Figure 13A:
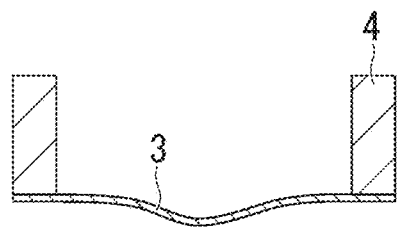
FIG. 13A is an explanatory view showing a particle capturing film before a tension application step in a method of producing a particle capturing device according to the third modified example of the embodiment.
Figure 13B:
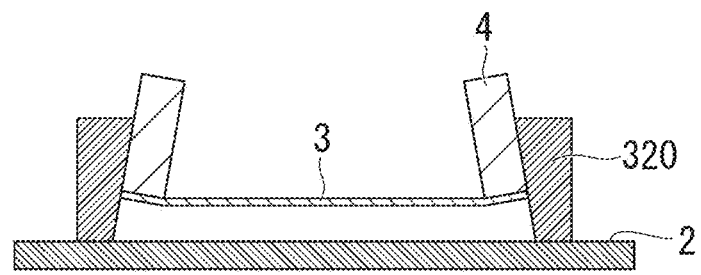
FIG. 13B is an explanatory view showing a step of bonding an inclination support member and a support to each other in the method of producing a particle capturing device according to the third modified example of the embodiment.

FIG. 12 is a cross-sectional view showing a particle capturing device 301 according to the third modified example of the embodiment. FIG. 12 is a view corresponding to FIG. 4.

As shown in FIG. 12, the particle capturing device 301 includes an inclination support member 320 which supports the support 4 in a state where the support 4 is inclined with respect to the substrate 2 such that the tension is applied to the particle capturing film 3. The inner surface of the inclination support member 320 is inclined with respect to a vertical line (a line perpendicular to one surface of the substrate 2). The inclination support member 320 supports the support 4 from the outside. An inner surface of the inclination support member 320 is inclined such that the upper end is positioned inward and the lower end is positioned outward. The support 4 of the third modified example does not have the concave portion 22 (see FIG. 4).

In the third modified example, in the tension application step, the tension is applied to the particle capturing film 3 such that the particle capturing film 3 is in parallel with the substrate 2 and the space 10 is formed between the particle capturing film 3 and the substrate 2. The deflection of the particle capturing film 3 before the tension application step is exaggerated in FIG. 13A, but the present invention is not limited thereto. Before the tension application step, the particle capturing film 3 may not be deflected.

In the tension application step, the support 4 is supported by the inclination support member 320 in a state where the support 4 is inclined with respect to the substrate 2 such that the tension is applied to the particle capturing film 3. Specifically, the outer surface of the support 4 is bonded to the inner surface of the inclination support member 320 fixed to the substrate 2 (see FIG. 13B). For example, the curable resin composition may be used as an adhesive.

According to the present modified example, the particle capturing device 301 includes the inclination support member 320 that supports the support 4 in a state where the support 4 is inclined with respect to the substrate 2 such that the tension is applied to the particle capturing film 3, and thus the following effects are exerted.

According to this configuration, it is possible to suppress deflection of the particle capturing film 3 with a simple configuration using the inclination support member 320.

Fourth Modified Example

Next, a fourth modified example of an embodiment will be described with reference to FIGS. 14, 15A, and 15B.

In the fourth modified example, the configuration for applying the tension to the particle capturing film 3 is particularly different from the configurations of the embodiments described above. In FIGS. 14, 15A, and 15B, the same configurations as those of the embodiments described above are denoted by the same reference numerals, and the detailed description thereof will not be provided.

Figure 14:
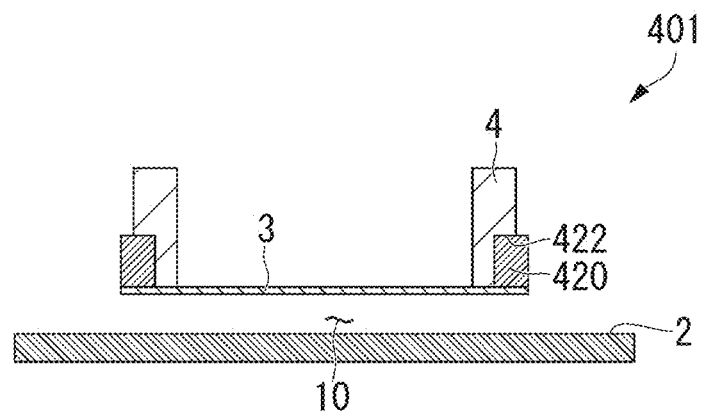
FIG. 14 is a cross-sectional view showing a particle capturing device according to a fourth modified example of an embodiment.
Figure 15A:
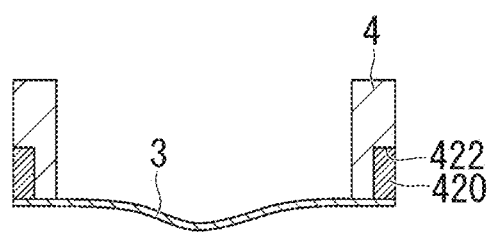
FIG. 15A is an explanatory view showing a particle capturing film before a tension application step in a method of producing a particle capturing device according to the fourth modified example of the embodiment.
Figure 15B:
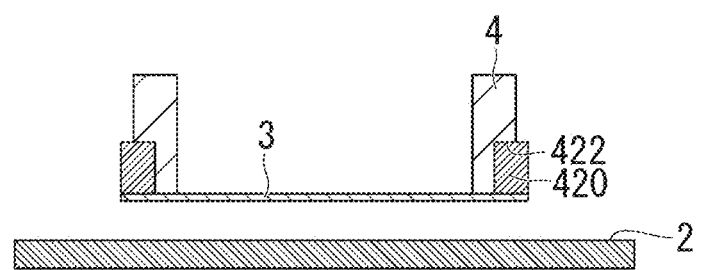
FIG. 15B is an explanatory view showing a swelling step of a liquid-absorbing swelling member in the method of producing a particle capturing device according to the fourth modified example of the embodiment.

FIG. 14 is a cross-sectional view showing a particle capturing device 401 according to the fourth modified example of the embodiment. FIG. 14 is a view corresponding to FIG. 4.

As shown in FIG. 14, the particle capturing device 401 includes a liquid-absorbing swelling member 420 which is bonded to the support 4 and increases in volume by absorbing a liquid such that the tension is applied to the particle capturing film 3. The liquid-absorbing swelling member 420 is attached to a concave portion 422 on the outside of the lower portion of the support 4. For example, examples of the material of the liquid-absorbing swelling member 420 include water-swelling rubber, polyurethane, and polyvinyl alcohol. Further, the material of the liquid-absorbing swelling member 420 is not particularly limited, and various materials can be employed as long as the materials have the property that the volume is increased by absorbing a liquid. The support 4 of the fourth modified example is connected to the substrate 2 by a connection member (not shown) such that the space 10 is formed between the particle capturing film 3 and the substrate 2.

In the fourth modified example, in the tension application step, the volume of the liquid-absorbing swelling member 420 is increased by allowing the liquid-absorbing swelling member 420 to absorb a liquid such that the particle capturing film 3 is in parallel with the substrate 2 and the space 10 is formed between the particle capturing film 3 and the substrate 2. The deflection of the particle capturing film 3 before the tension application step is exaggerated in FIG. 15A, but the present invention is not limited thereto. Before the tension application step, the particle capturing film 3 may not be deflected. Before the tension application step, the liquid-absorbing swelling member 420 has entered the concave portion 422 on the outside of the lower portion of the support 4.

In the tension application step, the volume of the liquid-absorbing swelling member 420 is increased by allowing the liquid-absorbing swelling member 420 to absorb a liquid such that the tension is applied to the particle capturing film 3. Specifically, the liquid-absorbing swelling member 420 is allowed to swell out of the concave portion 422 on the outside of the lower portion of the support 4 by allowing the liquid-absorbing swelling member 420 to absorb a liquid (see FIG. 15B).

According to the present modified example, the particle capturing device 401 includes the liquid-absorbing swelling member 420 which is bonded to the support 4 and increases in volume by absorbing a liquid such that the tension is applied to the particle capturing film 3, and thus the following effects are exerted.

According to this configuration, it is possible to suppress deflection of the particle capturing film 3 with a simple configuration using the liquid-absorbing swelling member 420.

Fifth Modified Example

Next, a fifth modified example of an embodiment will be described with reference to FIGS. 16, 17A, and 17B.

In the fifth modified example, the configuration for applying the tension to the particle capturing film 3 is particularly different from the configurations of the embodiments described above. In FIGS. 16, 17A, and 17B, the same configurations as those of the embodiments described above are denoted by the same reference numerals, and the detailed description thereof will not be provided.

Figure 16:
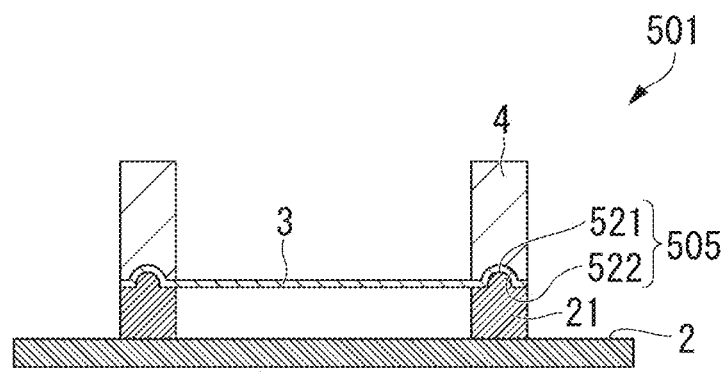
FIG. 16 is a cross-sectional view showing a particle capturing device according to a fifth modified example of an embodiment.
Figure 17A:
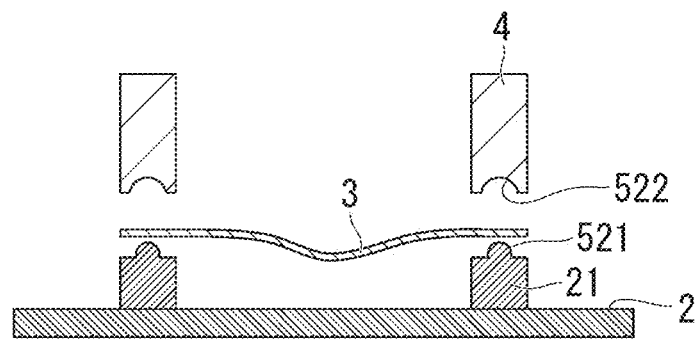
FIG. 17A is an explanatory view showing a particle capturing film before a tension application step in a method of producing a particle capturing device according to the fifth modified example of the embodiment.
Figure 17B:
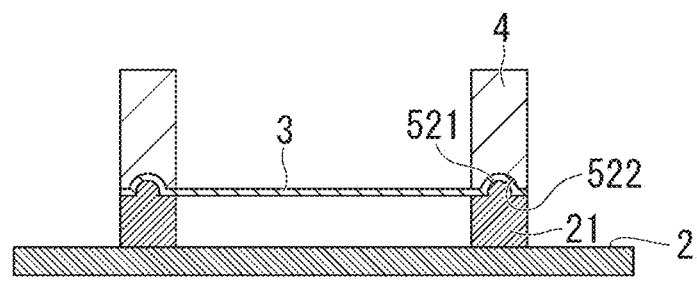
FIG. 17B is an explanatory view showing a fitting step of allowing a curved convex portion of a convex portion and a curved concave portion of a support to be fitted to each other in the method of producing a particle capturing device according to the fifth modified example of the embodiment.

FIG. 16 is a cross-sectional view showing a particle capturing device 501 according to the fifth modified example of the embodiment. FIG. 16 is a view corresponding to FIG. 4.

As shown in FIG. 16, the particle capturing device 501 includes a fitting structure 505 that allows the substrate 2 and the support 4 to be fitted to each other such that the tension is applied to the particle capturing film 3. The fitting structure 505 includes a curved convex portion 521 and a curved concave portion 522 that are fitted to each other. The fitting structure 505 is provided between the substrate 2 (the convex portion 21 provided on the substrate 2) and the support 4.

The curved convex portion 521 is provided on the convex portion 21 of the substrate 2. The curved convex portion 521 protrudes upward from the upper surface of the convex portion 21. The curved convex portion 521 has an upwardly projecting curved shape. For example, the curved convex portion 521 is formed of the same member as that of the convex portion 21 and integrated with the convex portion 21.

The curved concave portion 522 is provided in the lower surface of the support 4. The curved concave portion 522 has a curved shape along the curved convex portion 521.

In the fifth modified example, in the tension application step, the tension is applied to the particle capturing film 3 such that the particle capturing film 3 is in parallel with the substrate 2 and the space 10 is formed between the particle capturing film 3 and the substrate 2. The deflection of the particle capturing film 3 before the tension application step is exaggerated in FIG. 17A, but the present invention is not limited thereto. Before the tension application step, the particle capturing film 3 may not be deflected.

In the tension application step, the convex portion 21 and the support 4 are fitted to each other such that the tension is applied to the particle capturing film 3. Specifically, the curved concave portion 522 provided in the support 4 and the particle capturing film 3 are fitted to the curved convex portion 521 provided on the convex portion 21 (see FIG. 17B). For example, the particle capturing film 3 can be supported in a state where the tension is applied to the particle capturing film 3 by press-fitting the curved convex portion 521 and the particle capturing film 3 to the curved concave portion 522 of the support 4. In this manner, the convex portion 21, the particle capturing film 3, and the support 4 can be bonded to each other in a state where the tension is applied to the particle capturing film 3. For example, the curable resin composition may be used as an adhesive.

According to this modified example, in the particle capturing device 501, the fitting structure 505 includes the curved convex portion 521 provided on the convex portion 21 of the substrate 2 and the curved concave portion 522 provided in the support 4 and fitted to the curved convex portion 521, and thus the following effects are exerted.

According to this configuration, it is possible to suppress deflection of the particle capturing film 3 with a simple configuration using the curved convex portion 521 and the curved concave portion 522.

Other Modified Examples

The various shapes and the combinations of the constituent members shown in the above-described examples are merely examples, and various modifications can be made based on the design requirements and the like.

For example, in the embodiment described above, the fitting structure includes a convex portion provided on the substrate 2 and a concave portion provided in the support 4 and fitted to the convex portion, but the present invention is not limited thereto. For example, the fitting structure may include a convex portion provided on the support 4 and a concave portion provided in the substrate 2.

In the embodiment described above, the particle capturing film 3 includes the first layer 11 having the communication hole 13 and the second layer 12 which is connected to the communication hole 13 and has the through hole 14 having the same size as that of the outer shape of the capturing portion 15, but the present invention is not limited thereto. For example, the particle capturing film 3 may be a single layer having the capturing portion 15 and the communication hole 13.

In the embodiment described above, the space 10 is filled with a liquid, but the present invention is not limited thereto. For example, the space 10 may not be filled with a liquid.

Further, the respective constituent elements described in the embodiments or the modified examples thereof described above can be appropriately combined within a range not departing from the gist of the present invention, and some constituent elements among the plurality of combined components may not be used as appropriate.

EXAMPLES

Hereinafter, the present invention will be described in more detail based on the examples, but the present invention is not limited to the following examples.

Example (Production of Particle Capturing Film)

<<Patterning of Communication Holes>>

A silicon substrate was coated with a base agent using a spin coater (1500 rpm, 20 seconds) and prebaked on a hot plate at 90° C. for 1 minute and at 150° C. for 1 minute to form a base film.

The base film was coated with a photosensitive resin composition (see Japanese Unexamined Patent Application, First Publication Nos. 2008-180877 and 2011-111588) using a spin coater (1500 rpm, 20 seconds) and prebaked on a hot plate at 60° C. for 2 minutes. Thereafter, the film was subjected to pattern exposure (GH1 line, 150 mJ) using an i-line stepper (model "NSR-2205i14E", manufactured by Nikon Corporation) and heated on a hot plate at 90° C. for 3 minutes after the exposure. Thereafter, a development treatment was performed thereon for 30 seconds according to an immersion method using propylene glycol monomethyl ether acetate (PGMEA). Next, the developed resin pattern of the entire substrate was post-baked in an oven at 120° C. for 1 minute, thereby obtaining a cylindrical communication hole resin pattern having a diameter of 2 µm.

<<Patterning of Concave Portions>>

The communication hole resin pattern obtained in the above-described manner was coated with the photosensitive resin composition using a spin coater (1100 rpm, 60 seconds) and prebaked on a hot plate at 60° C. for 2 minutes and at 120° C. for 3 minutes. Thereafter, the communication hole resin pattern was subjected to pattern exposure (GH1 line, 60 mJ) using an i-line stepper (model "NSR-2205i14E", manufactured by Nikon Corporation) and heated on a hot plate at 120° C. for 3 minutes after the exposure. Thereafter, a development treatment was performed thereon for 2 minutes according to an immersion method using PGMEA. Next, the developed resin pattern of the entire substrate was post-baked in an oven at 180° C. for 15 minutes, thereby obtaining a concave portion pattern. The concave portions were patterned so as to have a regular hexagonal shape in which the distance between concave portions on the opposite sides was 25 µm.

(Peeling of Particle Capturing Film)

By immersing the particle capturing film with the patterned concave portions obtained in the above-described manner in a release agent and melting the base film, the particle capturing film in which the concave portion pattern was formed on the communication hole resin pattern was peeled off from the silicon substrate.

(Production of Substrate)

The substrate was formed by performing injection molding using a thermoplastic resin.

(Production of Support)

The support was formed by photo fabrication using a photocurable resin. The support was inclined such that the upper end of the inner surface of the support was positioned outward and the lower end of the inner surface of the support was positioned inward.

(Production of Expansion Member)

The expansion member was formed by photo fabrication using a photocurable resin. The expansion member was inclined such that the upper end of the outer surface of the lower portion of the expansion member was positioned outward and the lower end of the inner surface of the support was positioned inward. The outer shape of the lower portion of the expansion member was set to be larger than the inner shape of the support.

(Bonding of Particle Capturing Film and Substrate)

The support was bonded to the particle capturing film obtained in the above-described manner using an adhesive such that the surface with open concave portions was the upper surface. The support supporting the particle capturing film was expanded by press-fitting the expansion member to the support to which the particle capturing film was bonded. In this manner, the particle capturing film was supported by the support in a state where the tension was applied to the particle capturing film. The support was connected to the substrate using a curable resin composition such that the surface (the other surface) on a side opposite to the surface with open concave portions faced the substrate and a space was formed between the particle capturing film and the substrate. In this manner, a particle capturing device of the example in the shape shown in FIG. 8 (the shape of the first modified example) was obtained.

Comparative Example

A particle capturing device of a comparative example was prepared in the same manner as in the example except that the expansion member was press-fitted to the support to which the particle capturing film was bonded. The particle capturing device of the comparative example may not include the expansion member.

(Bonding of Particle Capturing Film and Substrate)

The support was bonded to the particle capturing film obtained in the above-described manner using an adhesive such that the surface with open concave portions was the upper surface. The support was connected to the substrate using a curable resin composition such that the surface (the other surface) on a side opposite to the surface with open concave portions faced the substrate and a space was formed between the particle capturing film and the substrate.

In this manner, a particle capturing device of the comparative example was obtained.

Experimental Example

Phosphate buffered saline was added to each of the particle capturing devices of the example and the comparative example and sucked by the suction unit so that the upper portion of the particle capturing film and the flow path between the particle capturing film and the substrate were filled with the phosphate buffered saline. Subsequently, an image was captured by focusing on the central portion of the particle capturing device using an inverted microscope (BZ-9000, manufactured by KEYENCE Corporation) equipped with a phase contrast objective lens at 20× magnification. Thereafter, an image of an edge portion of the particle capturing device was captured without focus correction.

Figure 18A:
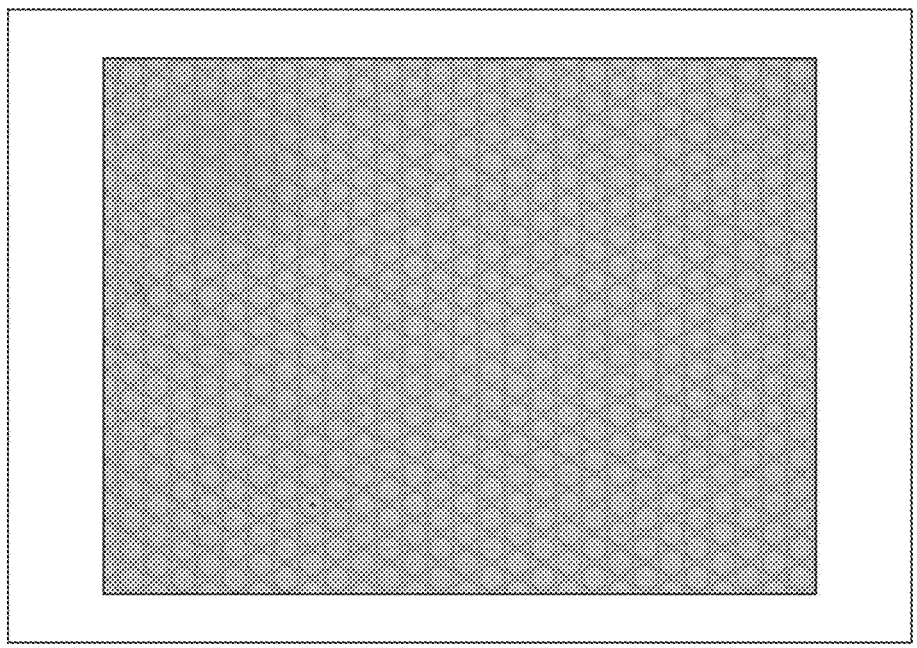
FIG. 18A is a photograph of a central portion of a particle capturing device, which shows results obtained by observing a particle capturing device of an example using a microscope.
Figure 18B:
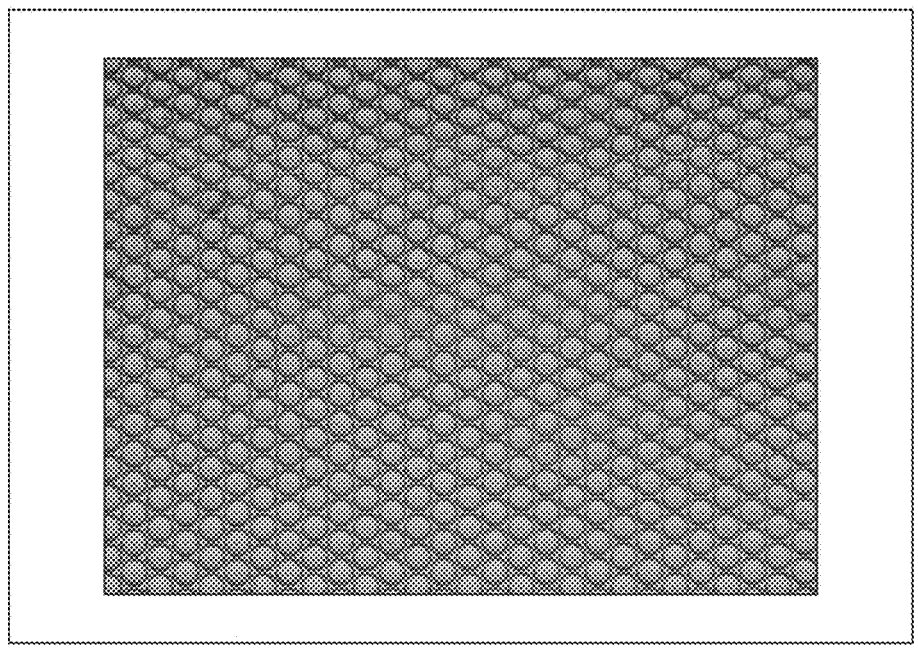
FIG. 18B is a photograph of an edge portion of the particle capturing device, which shows results obtained by observing the particle capturing device of the example using a microscope.
Figure 19A:
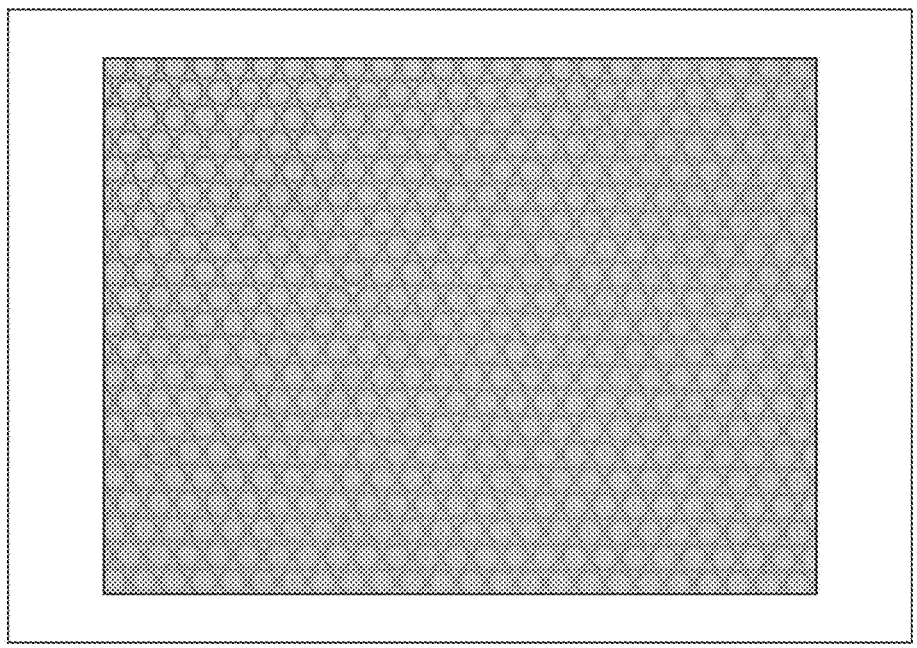
FIG. 19A is a photograph of a central portion of a particle capturing device, which shows results obtained by observing a particle capturing device of a comparative example using a microscope.
Figure 19B:
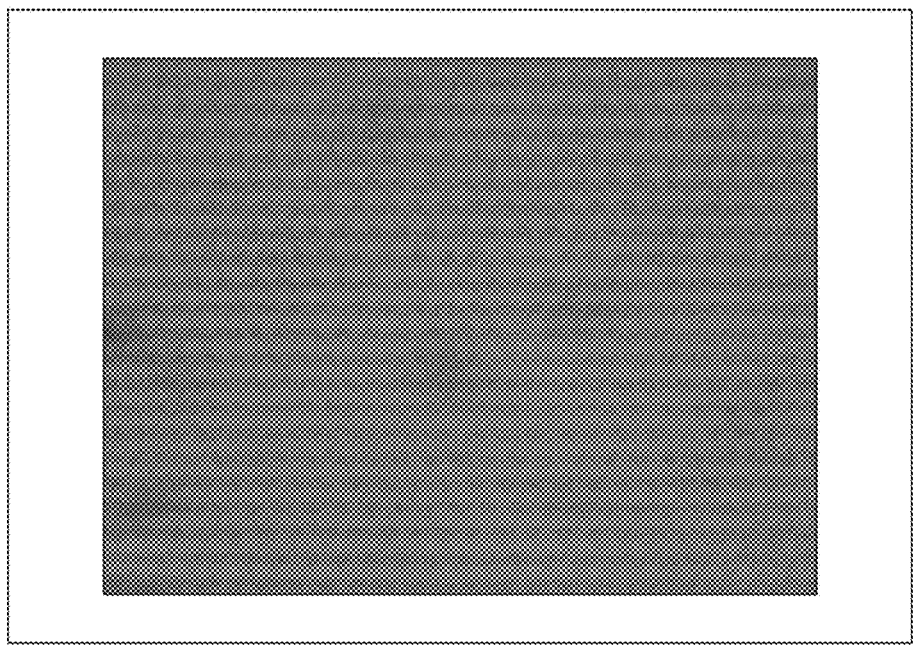
FIG. 19B is a photograph of an edge portion of the particle capturing device, which shows results obtained by observing the particle capturing device of the comparative example using a microscope.

FIGS. 18A and 18B are photographs showing the results obtained by observing the particle capturing device of the example using a microscope. FIG. 18A is a photograph of the central portion of the particle capturing device. FIG. 18B is a photograph of the edge portion of the particle capturing device. 19A and 19B are photographs showing the results obtained by observing the particle capturing device of the comparative example using a microscope. FIG. 19A is a photograph of the central portion of the particle capturing device. FIG. 19B is a photograph of the edge portion of the particle capturing device.

As shown in FIGS. 19A and 19B, in the particle capturing device of the comparative example, in a case where an image of the edge portion was captured after focusing on the central portion, defocusing occurred due to the influence of deflection of the particle capturing film.

On the contrary, as shown in FIGS. 18A and 19B, it was confirmed that deflection of the particle capturing film can be suppressed and thus occurrence of defocusing can be suppressed in the particle capturing device of the example.

Hereinbefore, the preferred examples of the present invention have been described, but the present invention is not limited to these examples. Additions, omissions, replacements, and modifications of configurations can be made in a range without departing from the gist of the present invention. The present invention is not limited by the foregoing description, but is limited only by the scope of the appended claims.

REFERENCE SIGNS LIST

1, 101, 201, 301, 401, 501: particle capturing device
2: substrate
3: particle capturing film
4: support
5: fitting structure
10: flow path (space)
11: first layer
12: second layer
13: communication hole
14: through hole
15: concave portion (capturing portion)
21: convex portion
22: concave portion
120: expansion member
220: film expansion member
320: inclination support member
420: liquid-absorbing swelling member
B: particle

The invention claimed is:
1. A particle capturing device comprising:
a substrate;
a particle capturing film configured to capture particles; and
a support configured to support the particle capturing film when tension is applied to the particle capturing film such that the particle capturing film is in parallel with the substrate and a space is formed between the particle capturing film and the substrate; and
an expansion member configured to expand the support such that the tension is applied to the particle capturing film.

2. A particle capturing device according to claim 1, wherein the expansion member is a film expansion member configured to expand the particle capturing film such that the tension is applied to the particle capturing film.

3. The particle capturing device according to claim 1, wherein the space is filled with a liquid.

4. The particle capturing device according to claim 1, wherein the particle capturing film includes a capturing portion having a size which enables capturing of one particle, and a communication hole having a size which does not allow passage of one particle and allowing the capturing portion and the space to communicate with each other.

5. The particle capturing device according to claim 4, wherein the particle capturing film includes a first layer having the communication hole, and a second layer which is connected to the communication hole and has a through hole having the same size as that of an outer shape of the capturing portion.

6. A particle capturing device, comprising:
a substrate;
a particle capturing film configured to capture particles;
a support configured to support the particle capturing film in a state of applying tension to the particle capturing film such that the particle capturing film is in parallel with the substrate and a space is formed between the particle capturing film and the substrate; and
an inclination support member configured to support the support in a state where the support is inclined with respect to the substrate such that the tension is applied to the particle capturing film.

7. The particle capturing device according to claim 6, wherein the space is filled with a liquid.

8. The particle capturing device according to claim 6, wherein the particle capturing film includes a capturing portion having a size which enables capturing of one particle, and a communication hole having a size which does not allow passage of one particle and allowing the capturing portion and the space to communicate with each other.

9. The particle capturing device according to claim 8, wherein the particle capturing film includes a first layer having the communication hole, and a second layer which is connected to the communication hole and has a through hole having the same size as that of an outer shape of the capturing portion.

10. A particle capturing device, comprising:
a substrate;
a particle capturing film configured to capture particles;
a support configured to support the particle capturing film in a state of applying tension to the particle capturing film such that the particle capturing film is in parallel with the substrate and a space is formed between the particle capturing film and the substrate; and
a liquid-absorbing swelling member configured to be bonded to the support and increase in volume by absorbing a liquid such that the tension is applied to the particle capturing film.

11. The particle capturing device according to claim 10, wherein the space is filled with a liquid.

12. The particle capturing device according to claim 10, wherein the particle capturing film includes a capturing portion having a size which enables capturing of one particle, and a communication hole having a size which does not allow passage of one particle and allowing the capturing portion and the space to communicate with each other.

13. The particle capturing device according to claim 12, wherein the particle capturing film includes a first layer having the communication hole, and a second layer which is connected to the communication hole and has a through hole having the same size as that of an outer shape of the capturing portion.

* * * * *